US011872175B2

(12) United States Patent
Mizera et al.

(10) Patent No.: US 11,872,175 B2
(45) Date of Patent: Jan. 16, 2024

(54) DEVICE FOR SUPPORTING AN ARM

(71) Applicant: Ottobock SE & Co. KGaA, Duderstadt (DE)

(72) Inventors: Oliver Mizera, Göttingen (DE); Jonas Bornmann, Duderstadt (DE); Thomas Bertels, Duderstadt (DE); Lukas Brünjes, Göttingen (DE)

(73) Assignee: OTTOBOCK SE & CO., KGAA, Duderstadt (DE)

( * ) Notice: Subject to any disclaimer, the term of this patent is extended or adjusted under 35 U.S.C. 154(b) by 444 days.

(21) Appl. No.: 16/347,702

(22) PCT Filed: Oct. 26, 2017

(86) PCT No.: PCT/EP2017/077492
§ 371 (c)(1),
(2) Date: May 6, 2019

(87) PCT Pub. No.: WO2018/083009
PCT Pub. Date: May 11, 2018

(65) Prior Publication Data
US 2019/0254910 A1  Aug. 22, 2019

(30) Foreign Application Priority Data
Nov. 7, 2016 (DE) ..................... 10 2016 121 202.4

(51) Int. Cl.
*A61H 1/02* (2006.01)
*B25J 9/00* (2006.01)
(Continued)

(52) U.S. Cl.
CPC ........... *A61H 1/0274* (2013.01); *A61B 90/60* (2016.02); *A61F 5/013* (2013.01); *B25J 9/0006* (2013.01);
(Continued)

(58) Field of Classification Search
CPC ....... A61B 90/60; A61B 90/53; A61F 5/0118; A61F 5/05866; A61F 5/3723;
(Continued)

(56) References Cited

U.S. PATENT DOCUMENTS 4,180,870 A * 1/1980 Radulovic ............... A61F 5/013
601/33
4,669,451 A * 6/1987 Blauth ...................... A61H 1/02
482/901

(Continued)

FOREIGN PATENT DOCUMENTS

DE          601 22 483 T2   3/2007
DE    10 2012 016 948 A1    3/2014
(Continued)

OTHER PUBLICATIONS

"FREEWHEEL" entry in Wikipedia; last edited Feb. 22, 2019, pp. 1-5.

*Primary Examiner* — Bradley H Philips
*Assistant Examiner* — Savannah L Gabriel
(74) *Attorney, Agent, or Firm* — WCF IP

(57) ABSTRACT

The present invention comprises a device for supporting at least one arm of a user, wherein the device has
at least one main body (2) for arranging on a torso (4) of the user and
at least one supporting device (8) for supporting the arm, wherein the supporting device (8) is arranged on the main body (2) via at least one joint (10) so that it can be moved relative to the main body (2),
wherein, in every position within a predetermined position range of the supporting system (8) relative to the main body (2), the joint (10) allows a movement of the supporting system (8) relative to the main body (2) in a first direction and prevents a movement in an opposite second direction.

21 Claims, 6 Drawing Sheets

Figure 1:
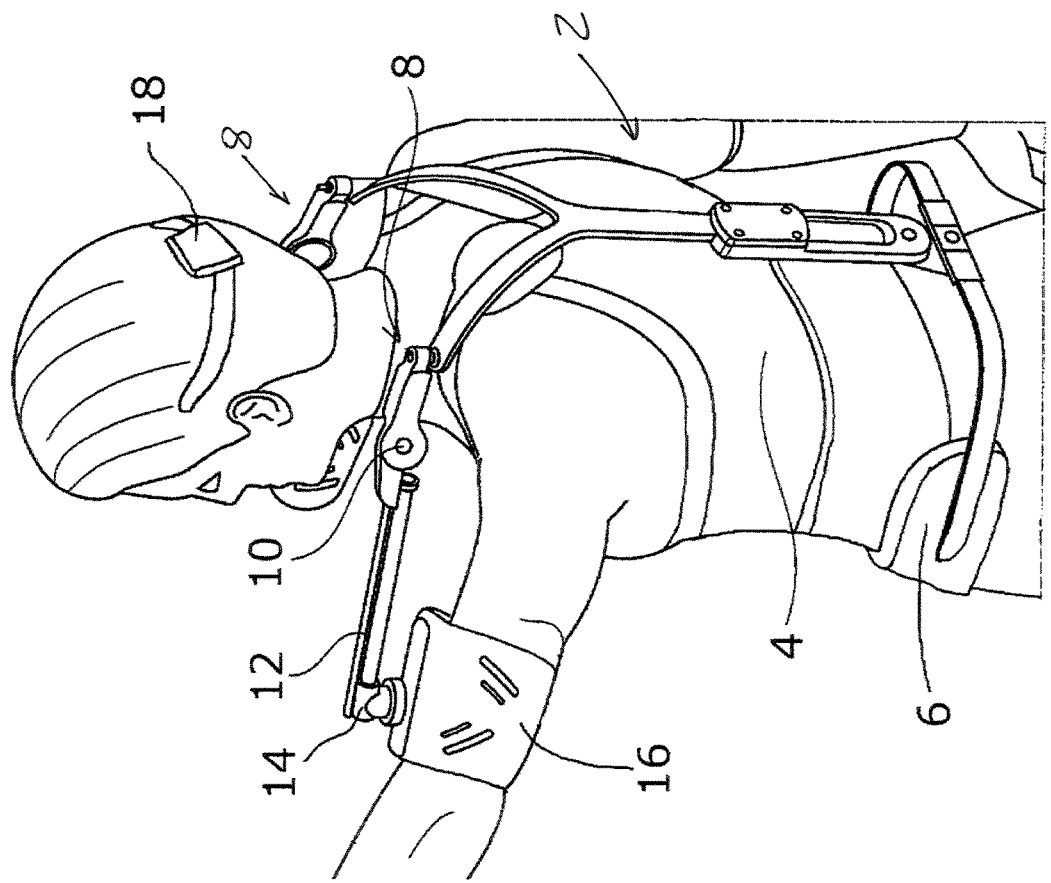

(51) Int. Cl.
*A61F 5/01* (2006.01)
*A61B 90/60* (2016.01)

(52) U.S. Cl.
CPC ............... *A61H 2201/1207* (2013.01); *A61H 2201/1638* (2013.01); *A61H 2201/5064* (2013.01)

(58) Field of Classification Search
CPC ............ A61F 5/3761; A61F 5/373; A61F 2005/0132; A61F 2005/0181; A61F 2005/0165; A61F 2005/0169; A41D 19/01582; A41D 19/01588; B25J 9/0006
See application file for complete search history.

(56) References Cited

U.S. PATENT DOCUMENTS

| | | | | |
|---|---|---|---|---|
| 6,500,138 B1 * | 12/2002 | Irby | ............... | A61F 5/0125 602/26 |
| 7,410,471 B1 * | 8/2008 | Campbell | ............ | A61F 5/0125 602/26 |
| 8,273,042 B2 * | 9/2012 | Lidolt | ............... | A61F 5/0125 602/5 |
| 8,764,850 B2 * | 7/2014 | Hansen | ............... | A61F 2/70 623/47 |
| 10,391,627 B2 * | 8/2019 | Van Engelhoven | ..... | B65H 1/10 |
| 11,020,247 B2 * | 6/2021 | Pomeroy | ............... | F16D 47/04 |
| 2010/0217163 A1 * | 8/2010 | Sankai | ............... | B25J 9/0006 601/5 |
| 2012/0172769 A1 * | 7/2012 | Garrec | ............... | A61F 5/013 601/33 |
| 2012/0184880 A1 * | 7/2012 | Doyle | ............... | A61F 5/0118 601/33 |
| 2014/0158839 A1 | 6/2014 | Doyle | | |
| 2019/0070058 A1 | 3/2019 | Kurzweg et al. | | |

FOREIGN PATENT DOCUMENTS

| | | | | |
|---|---|---|---|---|
| DE | 10 2016 104 880 A1 | 9/2017 | | |
| EP | 1 813 219 A1 | 8/2007 | | |
| EP | 2 380 529 A1 | 10/2011 | | |
| JP | 2014 172129 | * 9/2014 | ............ | A61F 5/013 |
| JP | 2017 184101 | * 10/2017 | ............ | A61F 2/54 |
| WO | 2012/099995 A2 | 7/2012 | | |
| WO | WO-2012099995 A2 * | 7/2012 | ............ | A61F 5/0118 |
| WO | 2014/195373 A1 | 12/2014 | | |

\* cited by examiner

DEVICE FOR SUPPORTING AN ARM

The invention relates to a device for supporting at least one arm of a user, said device having at least one main body for placement on a torso of the user and at least one supporting system for supporting the arm, wherein the supporting system is arranged on the main body to move relative to said main body by means of at least one joint.

This type of device is used to support and/or guide the arm of the user of the device, which is particularly useful for people who have to perform tasks above their heads or with extended and/or raised arms. For several years, orthopedic devices which aim to relieve and support at least one arm have been common, the intention of such devices being to provide relief so these people do not have to counteract the effective weight force over a long period of time with muscular strength alone. This type of device may also be designed as an orthopedic device.

For instance, WO 2012/099995 describes such a device, which comprises an arm support and corresponding compensation elements, wherein said compensation elements may comprise tensioned springs, for instance, and thereby permanently exert a force on the upper arm that pushes it upwards. This renders the work in what is otherwise a very uncomfortable position easier. The force applied by the spring elements serves to compensate the net weight of the arms. By adjusting the tension of the springs being used, the force applied prior to using the orthopedic device can be adjusted, for example to meet the needs of various wearers.

WO 2014/195373 describes a device which is intended to support a lifting and carrying of loads performed by the wearer of the device. It features passive force application elements, such as leaf springs or motor-driven actuators, which can be used, for instance, to fix certain supporting elements to one another and prevent a flexible movement which would otherwise be possible.

A supporting device is described in DE 10 2016 104 880, which has not been prepublished, that features the adjustment of a force, which is exerted by the device on the arm of the wearer, depending on a position of the head of the wearer of the device.

With most devices known from the prior art, the supportive effect is produced by the permanent application of a force on the arm that is to be supported. On the one hand, this means that this force must be overcome in order to move the arm in the respective opposite direction and on the other hand, that the force must continue to be applied to the arm, even when the arm is raised, and even in the event that the wearer of the device does not wish to change the position of the arm any further. This may be perceived as disruptive and uncomfortable.

The invention thus aims to eliminate or at least mitigate the disadvantages of the prior art.

The invention solves the task at hand by way of a device according to the generic term in claim 1, which is characterized by the fact that in every position within a predetermined position range of the supporting system relative to the main body, the joint allows a movement of the supporting system relative to the main body in a first direction and prevents it in an opposite second direction.

Unlike in WO 2012/099995 in particular, there is consequently no permanent application of force on the arm of the wearer of the device; rather, the joint is blocked in one direction of movement. The user, who works with raised arms for instance, can therefore place at least one arm on the at least one support device, without the supporting system being moved as a result, so long as the joint is configured to prevent the movement in this direction. However, a further raising of the arm can be achieved without difficulty, as the joint allows a movement in this direction.

The joint can preferably be unblocked in such a way that it allows a movement of the supporting system relative to the main body in the first direction and the second direction. This is an advantage when the device is to be taken off, for example, or the task performed with raised and/or extended arms has been completed. In this case, it must be possible to lower the arms, for example, and thereby move the joint in the second direction of movement, which is actually blocked. To this end, the joint can be operated in a second operating mode, in which the joint is unblocked and a movement in both directions allowed.

In a preferred configuration, the joint comprises a shaft and a wrap spring that interacts with the shaft. The rotational axis preferably runs in the symmetrical axis of the shaft, i.e. the longitudinal direction of the shaft, so the joint allows a rotation about said rotational axis. In this case, a rotation in the first direction is allowed, whereas the rotation in the second opposite direction is prevented by the joint. This is achieved in a structurally very simple manner by way of a wrap spring, which is preferably situated around the shaft. The wrap spring is preferably composed of several turns that guide around the shaft and are in contact with the shaft. Due to the friction between the material of the wrap spring and the exterior of the shaft of the joint, a force is exerted on the wrap spring during a swivelling of the supporting system relative to the main body, which results in a movement of the shaft relative to the wrap spring. If the movement is conducted in the first direction, this causes the diameter of the wrap spring to increase slightly, thereby enabling a movement of the shaft relative to the wrap spring. However, a swivelling of the at least one supporting system relative to the main body in the opposite direction results in the force exerted on the wrap spring by way of the friction, causing a reduction in the cross-section of the wrap spring, which results in an amplification of a clamping effect, said clamping effect being exerted on the shaft by the wrap spring. The stronger the torque applied in this direction or the force applied in this direction, the stronger the braking effect, said braking effect being caused solely by the friction between shaft and wrap spring. This is a self-amplifying brake. With this configuration, the operation of the joint in this mode does not require an electronic control system or a sensor.

The at least one supporting system is connected to the main body via the joint. A structural component that is connected to the main body and a second structural component that is connected to the supporting system thus form the joint, wherein the two structural components of the joint are moved relative to one another insofar as the supporting system is moved relative to the main body. In this case, the shaft is connected to one of the two structural components, i.e. either the main body or the supporting system, such that it is torque-proof, whereas the wrap spring is connected with the respective other structural component such that it is torque-proof. The shaft is preferably connected to the supporting system and the wrap spring to the main body such that they are torque-proof.

The device preferably features an actuator that is configured to stretch the loop, thereby unblocking the joint. To this end, the wrap spring preferably has an activation projection, which projects radially outwards from the symmetrical axis of the wrap spring and the symmetrical axis of the shaft, which is situated in the wrap spring. If a pressure is now applied to this projection in the tangential direction in relation to this axis, this leads to an expansion of the diameter of the wrap spring to such an extent that the self-amplifying braking effect is offset, so that in this state, the joint allows a movement of the shaft relative to the wrap spring and therefore also a movement of the at least one supporting system relative to the main body in both directions. For instance, the actuator may be a pin, a bolt or a rod, which can be moved longitudinally, for example, thereby exerting the necessary pressure on the projection of the wrap spring.

Alternatively or additionally, the joint comprises a magnetorheological fluid and at least one magnetic field generation device, such as an electromagnet, which is arranged in such a way that a magnetic field generated by the electromagnet has an effect on at least one part of the magnetorheological fluid. In particular, the magnetic field generation device features a coil made of a conductive material, the electromagnetic properties of which change upon being subjected to an electric current.

Magnetorheological fluids are fluids whose viscosity changes under the influence of a magnetic field. Conventionally, the viscosity of the magnetorheological fluid increases with an increasing magnetic field, causing the fluid to become less capable of flowing. An adjustable magnetic field can be generated by the at least one magnetic field generation device, so that the viscosity of the magnetorheological fluid is also adjustable. This allows for the construction of a joint which allows for the torque transmission to be influenced, for instance. As a result, the joint can be blocked or unblocked by the switching or deactivation of a magnetic field. A configuration of such a joint is described, for example, in DE 10 2010 055833 A1.

The system preferably has at least one directional sensor for determining the direction in which the supporting system is to be moved relative to the main body, and an electric control system, which is configured to control the magnetic field generation device depending on sensor data of the at least one directional sensor and thereby influence the generated magnetic field and adjust it to the required strength and direction, if necessary. To determine the movement of the supporting system relative to the main body, at least one torque and/or one bending sensor, for example, may be used. Alternatively or additionally, at least one acceleration, tilt and/or inertial sensor may be used for this purpose. Preferably, a force applied to the supporting system and especially on an arm shell of the supporting system is measured by way of at least one force and/or pressure sensor. These and/or other sensors allow for conclusions to be drawn concerning a movement that is either desired or has already been performed by the user of the system, said conclusions then being used for control purposes.

The sensor is thus able to determine the direction in which the at least one supporting system is to be moved relative to the main body by the user of the system. In this way, it is possible, for instance, to define the sign of a force that is exerted on the supporting system by the user. In this case, if the supporting system is to be moved in the first direction relative to the main body in which the joint allows the movement, the electric current that is fed to the electromagnet is adjusted in such a way that the magnetorheological fluid exhibits a viscosity that allows a movement of the joint. Depending on the structure of the joint, this may mean switching on or switching off of the electric current. However, if the sensor detects a force which would cause a movement of the supporting system relative to the main body in the second direction, in which the movement should be prevented, the electric control system is configured to control the magnetic field generation device such that the viscosity of the magnetorheological fluid is influenced in such a way that the joint is blocked.

If the joint is to be completely unblocked in order to allow a movement in both directions, only one operating mode of the electric current has to be adjusted correspondingly.

The electric control system is preferably configured to adjust and/or vary a strength of the electric current depending on the sensor data. This may be achieved, for example, in that the sensor not only identifies or determines the sign of a force applied to the supporting system by the user, but also the value of this force. Depending on the strength of the force, which causes a movement in the second direction, the electric control system can also adjust accordingly the strength of the electric current applied to the electromagnet, so as to ensure that a movement in this second direction is prevented. If the user of the system only places, for instance, his arm on the supporting system, it results in the exertion a force on the supporting system, which causes the supporting system to lower. The sensor detects this and the electric control system controls the electric current for the electromagnet such that the joint is blocked in this direction. This requires a current strength that is dependent on the weight of the arm. However, if during this action the user of the system is also holding a tool, for instance, the weight acting on the supporting system—and thus the force exerted—is considerably greater than it would be if there were no tool. Therefore, it may be beneficial to increase the strength of the electric current that is fed to the electromagnet.

In general, a movement in the second direction is deemed prevented when the forces acting on the device during normal operation are not sufficient to allow such a movement.

In a preferred configuration of the device, the magnetorheological fluid is situated in a gap and/or a channel between two structural components of the joints that can be moved relative to one another. In this case, it is enough to have a relatively low layer thickness, for example less than 1 mm, preferably less than 0.5 mm, to be able to perform the control. During the movement of the joint, natural gravitational forces occur in the magnetorheological fluid when the two structural components of the joint, which can be shifted or rotated against each other, move relative to one another. If the viscosity of the magnetorheological fluid is low, i.e. the fluid is highly capable of flowing, the magnetorheological fluid almost acts as a lubricant between the two structural components that are moving against one another and does not limit the movement, or only does so to a very small degree. However, if the viscosity is especially high, it blocks a movement of the two structural components in relation to one another; this enables a very effective and efficient blocking of the joint with a relatively low electric current.

The device preferably comprises at least one permanent magnet, the magnetic field of which also has an effect on at least one part of the magnetorheological fluid. The viscosity of the magnetorheological fluid is increased by the magnetic field of the permanent magnet, meaning that the joint is blocked when there is no electric current available. If the electromagnet is now subjected to an electric current, this either causes—depending on the direction of the resulting magnetic field—an amplification of the block, which is an advantage, for instance, when a sensor detects an especially strong effect of the torque; or a reduction of the magnet field acting on the fluid, which allows for the joint to be unblocked in this direction of movement.

With all the configurations described here, it is an additional advantage that the joint can also be unblocked when it is subjected to a load. This is particularly advantageous when it is being used at the workplace, as no unnatural, additional movements need to be executed to relieve the joint of a load before it can be unblocked.

In order to fully unblock the joint and switch to the second operating mode, a range of possibilities can be implemented. For example, an electrical contact, which may be available in a glove worn on the hand, can be made by placing two fingers on top of one another, thereby signalling that the joint is to be unblocked. This can cause the activation of, for instance, an actuator that acts on the projection of the wrap spring.

Of course, there are other possibilities to effect control, for example via a movement of a body part, such as the head, or a voice command.

The joint preferably has at least one freewheel and/or one ratchet mechanism, which are used to ensure that the joint can be moved freely in the at least one direction. Of course, such freewheels or ratchet mechanisms can also be combined with magnetorheological and/or electrorheological fluids.

If a permanent magnet is used to constantly subject a magnetorheological fluid to a magnetic field, the permanent magnet can also be moved, for example rotated, to control the joint, so that the part of the magnetic field generated by the permanent magnet that is acting on the magnetorheological fluid changes and the joint can thus be switched. Of course, this is also conceivable for electrorheological fluids with an electric field generation device.

The joint preferably features an electrorheological fluid and at least one electric field generation device for generating an electric field, which is arranged such that an electric field generated by the electric field generation device also acts on at least one part of the electrorheological fluid.

Figure 2:
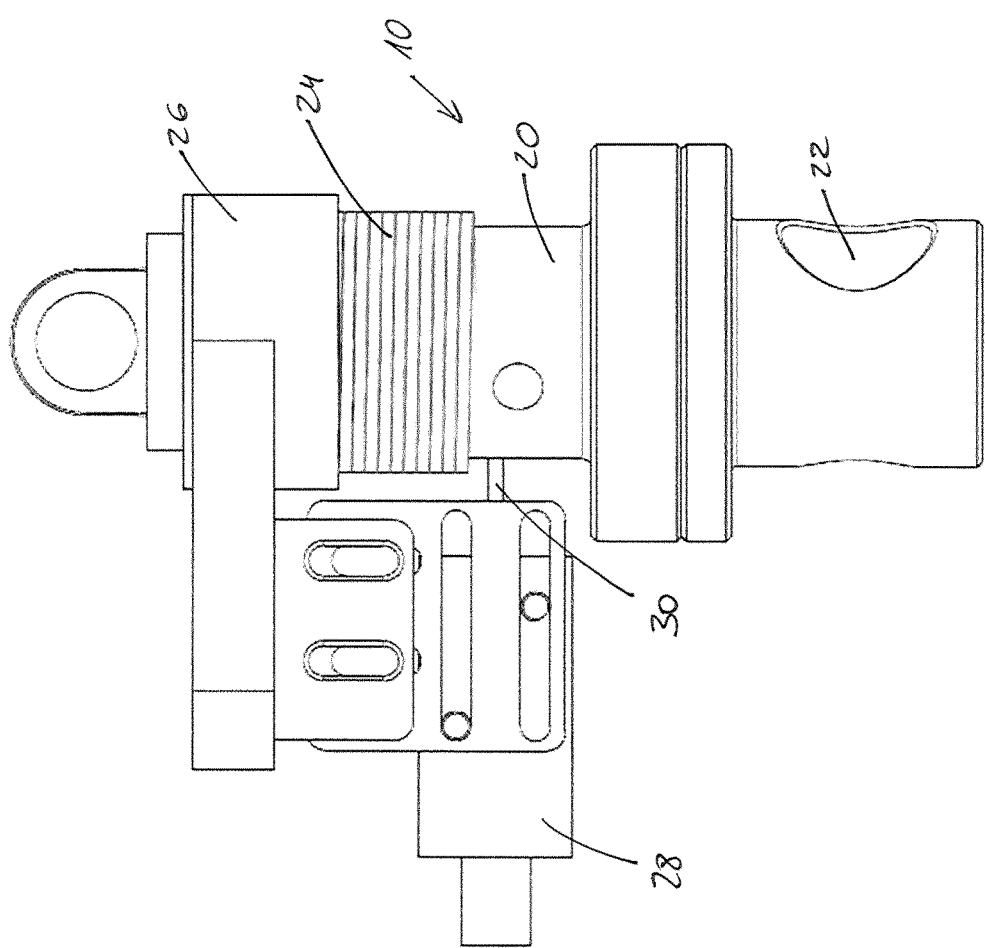
Figure 3:
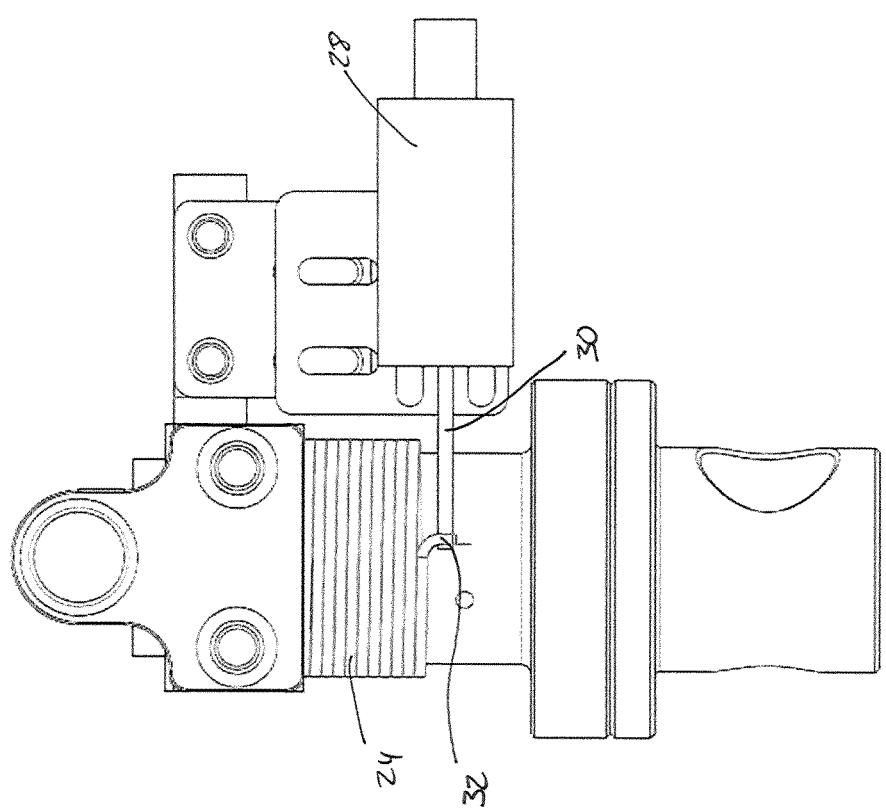
Figure 4:
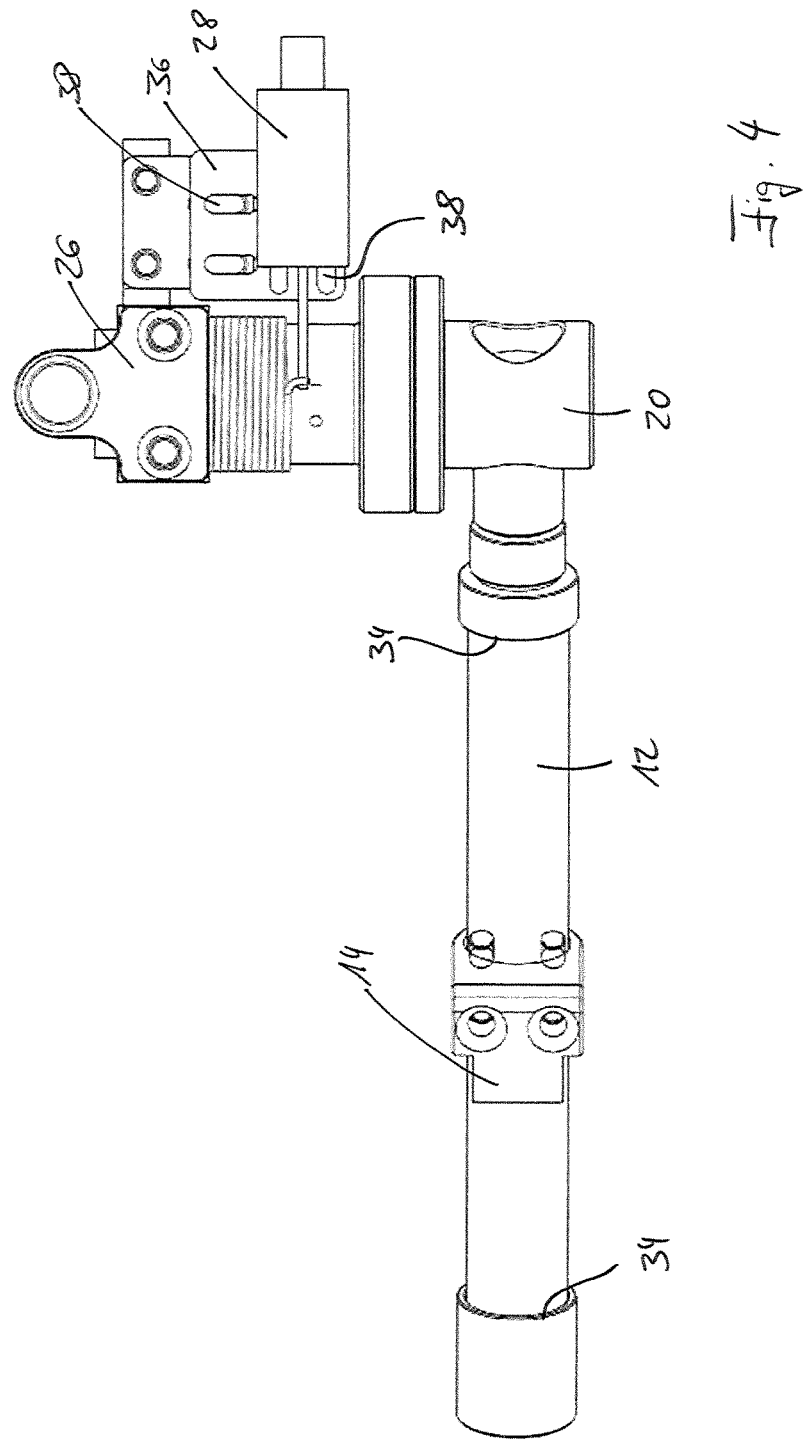
Figure 5:
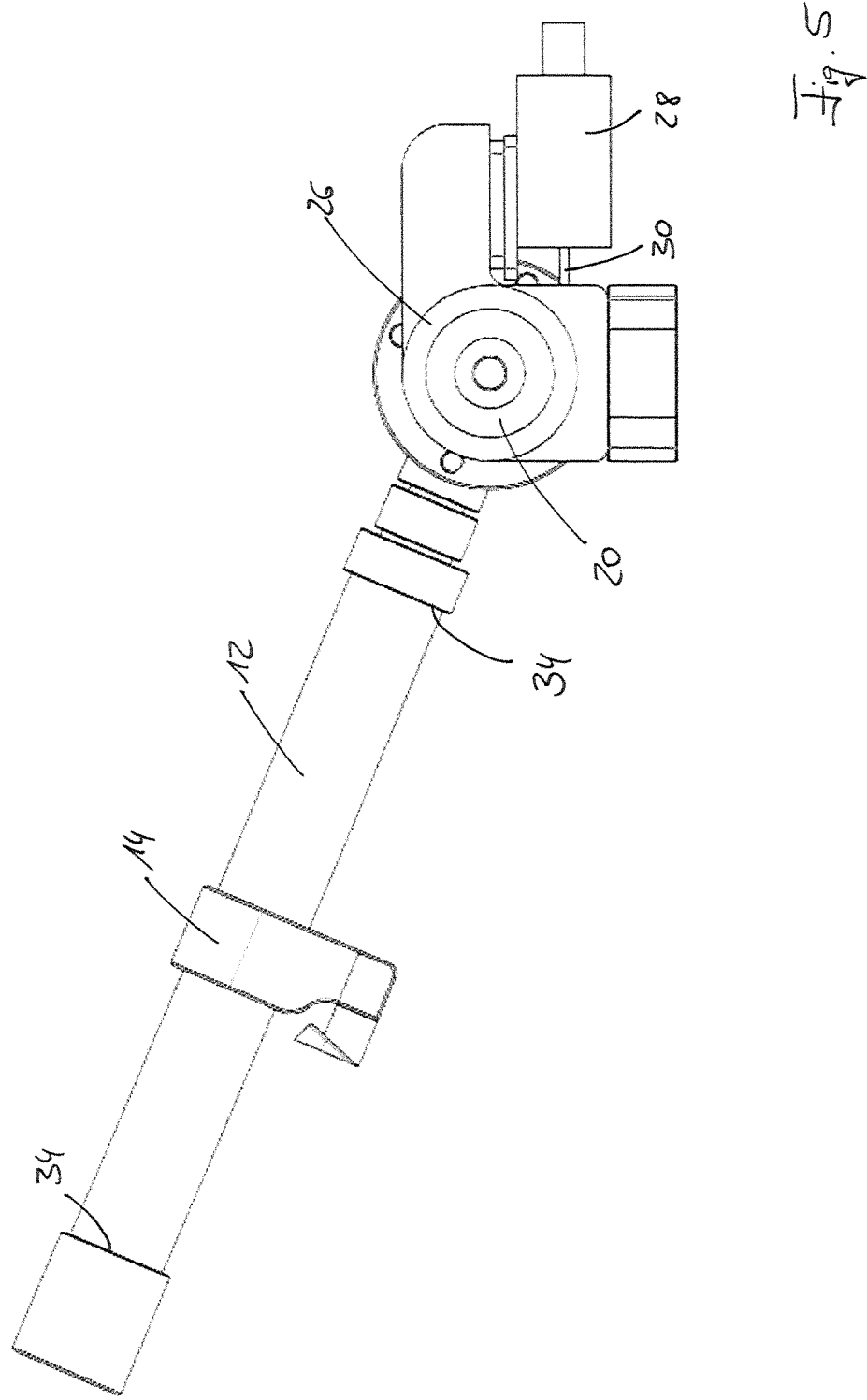
Figure 6:
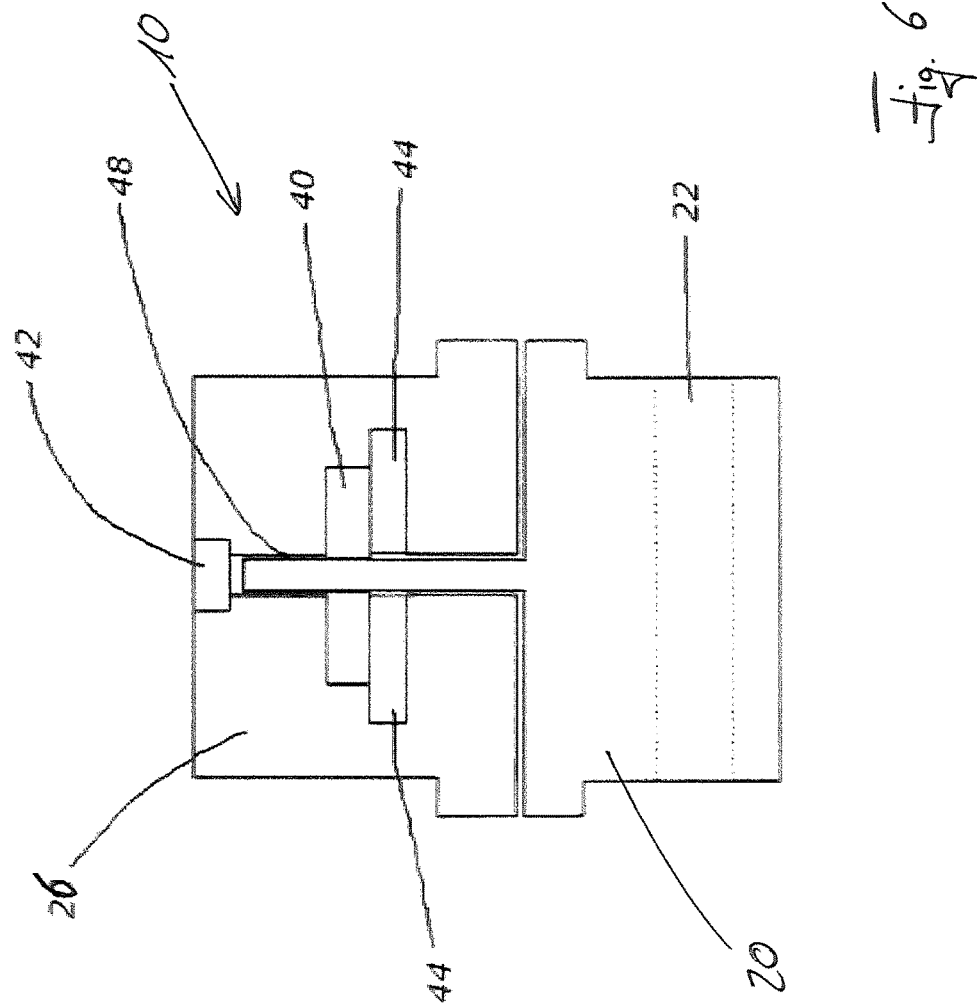

In the following, an example of an embodiment of the present invention will be explained in more detail by way of the attached drawings. They show:

FIG. 1—an orthopedic device according to a first example of an embodiment of the present invention when in the mounted state, FIG. 2—the schematic depiction of a joint for an orthopaedic device according to another example of an embodiment of the present invention, FIG. 3—the joint from FIG. 2 from another perspective, FIG. 4—the image from FIG. 3 with the part of a supporting system, FIG. 5—the image from FIG. 4 from another perspective, FIG. 6—a schematic sectional view through a joint.

FIG. 1 shows an orthopedic device according to a first example of an embodiment of the present invention when in the mounted state. It has a main body 2, which is designed in the form of belts and holding rails and is arranged on the torso 4 of the wearer of the device. The required stability is achieved with a pelvic strap 6. It also acts as a force transmission element.

The device features two supporting systems 8, each of which comprises a joint 10, on which a telescopic rod 12 is arranged. A slide element 14 is situated on said telescopic rod; the arm shell 16 is situated on said slide element.

The arm shown on the left-hand side of FIG. 1 is depicted in the raised state. The telescopic rod 12 has been inserted and the slide element 14 is therefore positioned relatively close to the shoulder of the wearer. A lowering of the arm out of this position would lead to a swivelling of the joint 10, which corresponds to a movement in the second direction. This is prevented by the joint 10, insofar as it is not unblocked. The wearer wears a head element 18, which comprises an angle of inclination sensor in the example of an embodiment shown. With said sensor, the angle of inclination or the position of the head of the wearer can be determined. Using the data identified by the sensor, an electric control system—not depicted—is able to switch the respective joint 10 out of the first operating mode, in which the movement of the joint is only allowed in the first direction and is prevented in the second direction, into the second operating mode, in which the joint is unblocked and a movement in both directions is allowed.

FIG. 2 depicts an enlarged view of the joint 10. It features a shaft 20, which has a bore 22 into which the telescopic rod 12 can be inserted. The shaft 20 is thus connected to the supporting system 8 such that it is torque-proof. The joint 10 shown in FIG. 2 also comprises a wrap spring 24, which extends around the shaft 20 in several turns. It is connected to a structural component 26 such that it is torque-proof, said structural component forming the connection to the main body 2.

If the shaft 20 is now rotated about its longitudinal axis, a force is exerted on the wrap spring 24 by way of the friction between the wrap spring 24 and the shaft 20; this results in a reduction or expansion of the cross-section, i.e. of the diameter of the turns of the wrap spring 24. This enables either the movement, since the diameter of the wrap spring 24 increases, or blocks the joint, since the movement results in a reduction in the diameter of the wrap spring 24.

The joint 10 shown in FIG. 2 also features an actuator 28, which comprises a pin 30, wherein said pin can be moved right and left in the example of an embodiment shown.

FIG. 3 shows that the pin 30 of the actuator 28 interacts with a projection 32 of the wrap spring 24. If the pin 30 of the actuator 28 is moved, the projection 32 in the example of an embodiment shown moves to the left, which causes the cross-section of the wrap spring 24 to expand, thereby releasing the joint.

FIG. 4 shows the image from FIG. 3 with a telescopic rod 12 arranged on the shaft 20. The slide element 14 is situated on said telescopic rod, wherein the slide element is mounted on the telescopic rod 12 between two end stops 34 such that it can be shifted.

The actuator 28 is connected to the structural component 26 via a mounting plate 36. The position of the actuator 28 relative to the structural component 26 can be individually adjusted via elongated holes 38 in such a way that the pin 30 interacts with the projection 32.

FIG. 5 shows the arrangement from FIG. 4 from another perspective. The shaft 20 is clearly shown, said shaft being situated in the structural component 26 such that it can be rotated. The slide element 14, which is mounted such that it can be shifted, is situated on the telescopic rod 12; the movement of said slide element is restricted by the two end stops 34. The arm shell 16, not depicted in FIG. 5, can be arranged on said slide element.

FIG. 6 shows a schematic sectional view through the joint 10. The bore 22 can be clearly recognized, which is situated on the shaft 20, i.e. on the structural component of the joint 10 that is mounted so it can be rotated. There is a recess on the structural component 26, in which a pin of the shaft 20 is arranged. A permanent magnet 42 is located at the end. There is a hollow space inside the structural component 26, inside of which a magnetorheological fluid 40 and a magnetic field generation device 44, such as an electromagnet, are located. In the example of an embodiment shown, the magnetorheological fluid 40 is subjected to the magnetic field of the permanent magnet 42, such that its viscosity increases and is therefore less capable of flowing. The joint is thus blocked, since the shaft 20 cannot be moved relative to the structural component 26. However, if a magnetic field is built up by the magnetic field generation device 44, said magnetic field opposing the magnetic field of the permanent magnet 42, the two magnetic fields cancel each another out in terms of their effect and the magnetorheological fluid becomes considerably less viscous and is thus much more capable of flowing, so that the two structural components 20, 26 can be moved relative to one another. The magnetorheological fluid 40 is found in both the previously mentioned hollow space and in a gap 48.

REFERENCE LIST 2 main body
4 torso
6 pelvic belt
8 supporting system
10 joint
12 telescopic rod
14 slide element
16 arm shell
18 head element
20 shaft
22 bore
24 wrap spring
26 structural component
28 actuator
30 pin
32 projection
34 end stop
36 mounting plate
38 elongated hole
40 magnetorheological unit
42 permanent magnet
44 magnetic field generation device
48 gap

The invention claimed is:

1. A device for supporting at least one arm of a user, comprising:
   at least one main body for arranging on a torso of the user; and
   at least one supporting device for supporting the at least one arm,
      wherein the at least one supporting device comprises at least one joint and at least one telescopic rod connected to the at least one joint,
      wherein the at least one supporting device is arranged on the at least one main body via the at least one joint so that the at least one supporting device is moveable relative to the at least one main body and is positionable over at least the top of one shoulder,
      wherein, in every position within a predetermined position range of the at least one supporting device relative to the at least one main body, the at least one joint is blockable such that the at least one joint allows a movement of the at least one supporting device relative to the at least one main body in a first direction and prevents all movement of the at least one supporting device in a second direction opposite the first direction,
      wherein the at least one joint is unblockable without any movements of the at least one joint.

2. The device according to claim 1, wherein the at least one joint is unblockable in such a way that the at least one joint allows a movement of the at least one supporting device relative to the at least one main body in the first direction and the second direction.

3. The device according to claim 1, wherein the at least one joint comprises a shaft and a wrap spring, wherein the wrap spring interacts with the shaft.

4. The device according to claim 3, further comprising an actuator configured to expand the wrap spring and thereby unblock the at least one joint.

5. The device according to claim 1 wherein the at least one joint comprises a magnetorheological fluid and at least one magnetic field generation device, wherein the at least one magnetic field generation device is arranged to generate a magnetic field which has an effect on at least one part of the magnetorheological fluid.

6. The device according to claim 5, further comprising:
   at least one directional sensor for determining a direction in which the at least one supporting device is to be moved relative to the at least one main body; and
   an electric control system configured to control the at least one magnetic field generation device depending on sensor data from the at least one directional sensor.

7. The device according to claim 6, wherein the electric control system is configured to adjust and/or vary the magnetic field generated by the at least one magnetic field generation device depending on the sensor data.

8. The device according to claim 5 wherein the magnetorheological fluid is situated in a gap and/or a channel between two structural components of the at least one joint, wherein the two structural components are moveable relative to one another.

9. The device according to claim 5 further comprising at least one permanent magnet which produces a magnetic field which acts on at least one part of the magnetorheological fluid.

10. The device according to claim 5 wherein the at least one magnetic field generation device comprises at least one electromagnet.

11. The device of claim 1 further comprising at least one slide element which slides on the at least one telescopic rod, and at least one arm shell connected to the at least one slide element.

12. A device for supporting at least one arm of a user, comprising:
   at least one main body for arranging on a torso of the user; and
   at least one supporting device for supporting the at least one arm,
      wherein the at least one supporting device comprises at least one joint,
      wherein the at least one supporting device is arranged on the at least one main body so that the at least one joint is positionable over the top of at least one shoulder of the user,
      wherein the at least one supporting device is arranged on the at least one main body via the at least one joint so that the at least one supporting device is moveable relative to the at least one main body,
      wherein, in every position within a predetermined position range of the at least one supporting device relative to the at least one main body, the at least one joint is blockable such that the at least one joint allows a movement of the at least one supporting device relative to the at least one main body in a first direction and prevents all movement of the at least one supporting device in a second direction opposite the first direction,
      wherein the at least one joint is unblockable without any movements of the at least one joint.

13. The device according to claim 12, wherein the at least one joint is unblockable in such a way that the at least one joint allows a movement of the at least one supporting device relative to the at least one main body in the first direction and the second direction.

14. The device according to claim 12, wherein the at least one joint comprises a shaft and a wrap spring, wherein the wrap spring interacts with the shaft.

15. The device according to claim 14, further comprising an actuator configured to expand the wrap spring and thereby unblock the at least one joint.

16. The device of claim 12 further comprising at least one telescopic rod connected to the at least one joint, and at slide element which slides on the at least one telescopic rod, and at least one arm shell connected to the at least one slide element.

17. A device for supporting at least one arm of a user, comprising:
   at least one main body for arranging on a torso of the user; and
   at least one supporting device for supporting the at least one arm,
      wherein the at least one supporting device comprises at least one joint and at least one telescopic rod connected to the at least one joint,
      wherein the at least one supporting device is arranged on the at least one main body so that the at least one joint is positionable over the top of at least one shoulder of the user and the at least one telescopic rod extends over the at least one arm,
      wherein the at least one supporting device is arranged on the at least one main body via the at least one joint so that the at least one supporting device is moveable relative to the at least one main body,
      wherein, in every position within a predetermined position range of the at least one supporting device relative to the at least one main body, the at least one joint is blockable such that the at least one joint allows a movement of the at least one supporting device relative to the at least one main body in a first direction and prevents all movement of the at least one supporting device in a second direction opposite the first direction,
      wherein the at least one joint is unblockable without any movements of the at least one joint.

18. The device according to claim 17, wherein the at least one joint is unblockable in such a way that the at least one joint allows a movement of the at least one supporting device relative to the at least one main body in the first direction and the second direction.

19. The device according to claim 17, wherein the at least one joint comprises a shaft and a wrap spring, wherein the wrap spring interacts with the shaft.

20. The device according to claim 19, further comprising an actuator configured to expand the wrap spring and thereby unblock the at least one joint.

21. The device of claim 17 further comprising at slide element which slides on the at least one telescopic rod, and at least one arm shell connected to the at least one slide element.

* * * * *